(12) United States Patent
Narula et al.

(10) Patent No.: US 8,785,677 B1
(45) Date of Patent: Jul. 22, 2014

(54) ORGANOLEPTIC COMPOUND

(71) Applicants: Anubhav P. S. Narula, Hazlet, NJ (US); Richard A. Weiss, Livingston, NJ (US); James Anthony Lasome, Matawan, NJ (US)

(72) Inventors: Anubhav P. S. Narula, Hazlet, NJ (US); Richard A. Weiss, Livingston, NJ (US); James Anthony Lasome, Matawan, NJ (US)

(73) Assignee: International Flavors & Fragrances Inc., New York, NY (US)

( * ) Notice: Subject to any disclaimer, the term of this patent is extended or adjusted under 35 U.S.C. 154(b) by 0 days.

(21) Appl. No.: 13/775,380

(22) Filed: Feb. 25, 2013

(51) Int. Cl.
*C07C 69/56* (2006.01)
(52) U.S. Cl.
USPC ............................................ 560/205; 512/26
(58) Field of Classification Search
USPC ............................................ 560/205; 512/26
See application file for complete search history.

(56) References Cited

U.S. PATENT DOCUMENTS 3,709,929 A * 1/1973 Exner et al. ................... 560/205
7,632,964 B2 12/2009 Furrer et al.
2007/0298994 A1* 12/2007 Finke et al. ....................... 512/1

OTHER PUBLICATIONS

Sturm, Wolfgang, "Systematic synthesis of odoriferous substances. Odor relations of the isobutenyl and phenyl groups" Parfuemerie und Kosmetik (1974), 55(12), 351-355.
English Abstract.

* cited by examiner

*Primary Examiner* — John Hardee
(74) *Attorney, Agent, or Firm* — Elizabeth M. Quirk; XuFan Tseng; Joseph F. Leightner

(57) ABSTRACT

The present invention is directed to a novel compound, but-2-enoic acid 1,2-dimethyl-butyl ester, and a method of improving, enhancing or modifying a fragrance formulation through the addition of an olfactory acceptable amount of but-2-enoic acid 1,2-dimethyl-butyl ester.

9 Claims, No Drawings

ORGANOLEPTIC COMPOUND

FIELD OF THE INVENTION

The present invention relates to a novel compound and its incorporation and use as a fragrance material.

BACKGROUND OF THE INVENTION

There is an ongoing need in the fragrance industry to provide new chemicals to give perfumers and other persons the ability to create new fragrances for perfumes, colognes and personal care products. Those with skill in the art appreciate how small differences in chemical structures can result in unexpected and significant differences in odor, notes and characteristics of molecules. These variations allow perfumers and other persons to apply new compounds in creating new fragrances.

SUMMARY OF THE INVENTION

The present invention provides a novel compound but-2-enoic acid 1,2-dimethyl-butyl ester and its unexpected advantageous use in enhancing, improving or modifying the fragrance of perfumes, colognes, toilet waters, personal products, fabric care products, and the like.

One embodiment of the present invention is directed to but-2-enoic acid 1,2-dimethyl-butyl ester, a novel fragrance compound, represented by the following formula:

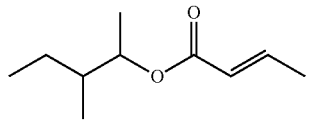

Structure I

Another embodiment of the present invention is directed to the use of but-2-enoic acid 1,2-dimethyl-butyl ester as a fragrance material in perfumes, colognes, toilet waters, personal products, fabric care products, and the like.

Another embodiment of the present invention is directed to a fragrance composition comprising but-2-enoic acid 1,2-dimethyl-butyl ester.

Another embodiment of the present invention is directed to a fragrance product comprising but-2-enoic acid 1,2-dimethyl-butyl ester.

Another embodiment of the present invention is directed to a method of improving, enhancing or modifying a fragrance formulation by incorporating an olfactory acceptable amount of but-2-enoic acid 1,2-dimethyl-butyl ester.

These and other embodiments of the present invention will be apparent by reading the following specification.

DETAILED DESCRIPTION OF THE INVENTION

It has been surprisingly found that but-2-enoic acid 1,2-dimethyl-butyl ester possesses unexpected strong and complex notes with a unique fruity and sweet combination.

But-2-enoic acid 1,2-dimethyl-butyl ester of the present invention is represented by the following structure:

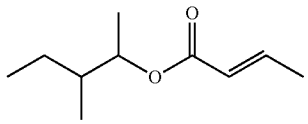

Structure I

But-2-enoic acid 1,2-dimethyl-butyl ester can be prepared according to the following reaction scheme, the details of which are specified in the Examples. The reagents were purchased from Aldrich Chemical Company unless noted otherwise.

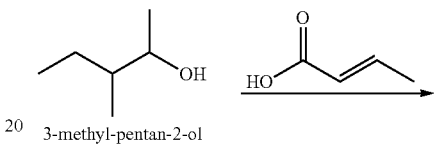

3-methyl-pentan-2-ol

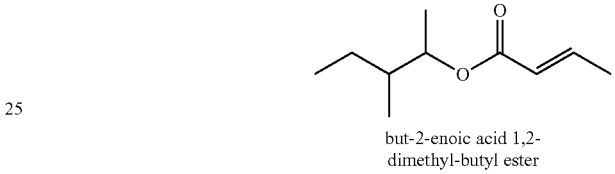

but-2-enoic acid 1,2-dimethyl-butyl ester

Complexity of odor notes refers to the presence of multiple and/or mixed but defined odors rather than a single note or a few easily identifiable notes. High levels of complexity are also assigned to compounds that possess ambiguous and somehow hard-to-define notes because of direct contribution or the many olfactive combinations of odors produced. Fragrance materials of high level complexity are considered having unusual and high quality.

The use of the compound of the present invention is widely applicable in current perfumery products, including the preparation of perfumes and colognes, the perfuming of personal care products such as soaps, shower gels, and hair care products, fabric care products as well as air fresheners and cosmetic preparations. This compound can also be used to perfume cleaning agents, such as, but not limited to detergents, dishwashing materials, scrubbing compositions, window cleaners and the like. In these preparations, the compound of the present invention can be used alone or in combination with other perfuming compositions, solvents, adjuvants and the like. The nature and variety of the other ingredients that can also be employed are known to those with skill in the art.

Many types of fragrances can be employed in the present invention, the only limitation being the compatibility with the other components being employed. Suitable fragrances include but are not limited to fruits such as almond, apple, cherry, grape, pear, pineapple, orange, strawberry, raspberry; musk; and flower scents such as lavender-like, rose-like, iris-like, carnation-like. Other pleasant scents include herbal and woodland scents derived from pine, spruce and other forest smells. Fragrances may also be derived from various oils, such as essential oils, or from plant materials such as peppermint, spearmint and the like.

A list of suitable fragrances is provided in U.S. Pat. No. 4,534,891, the contents of which are incorporated by reference as if set forth in its entirety. Another source of suitable fragrances is found in *Perfumes, Cosmetics and Soaps*, Second Edition, edited by W. A. Poucher, 1959. Among the fragrances provided in this treatise are acacia, cassie, chypre, cyclamen, fern, gardenia, hawthorn, heliotrope, honeysuckle, hyacinth, jasmine, lilac, lily, magnolia, mimosa, narcissus, freshly-cut hay, orange blossom, orchid, reseda, sweet pea, trefle, tuberose, vanilla, violet, wallflower, and the like.

The compound of the present invention can be used in combination with a complementary fragrance compound. The term "complementary fragrance compound" as used herein is defined as a fragrance compound selected from the group consisting of 2-[(4-methylphenyl)methylene]-heptanal (Acalea), iso-amyl oxyacetic acid allylester (Allyl Amyl Glycolate), (3,3-dimethylcyclohexyl)ethyl ethyl propane-1,3-dioate (Applelide), 2-ethyl-4-(2,2,3-trimethyl-3-cyclopenten-1-yl)-2-buten-1-ol (Bacdanol), 2-methyl-3-[(1,7,7-trimethylbicyclo[2.2.1]hept-2-yl)oxy]exo-1-propanol (Bornafix), 1,2,3,5,6,7-hexahydro-1,1,2,3,3-pentamethyl-4H-inden-4-one (Cashmeran), 1,1-dimethoxy-3,7-dimethyl-2,6-octadiene (Citral DMA), 3,7-dimethyl-6-octen-1-ol (Citronellol), 3A,4,5,6,7,7A-hexahydro-4,7-methano-1H-inden-5/6-yl acetate (Cyclacet), 3A,4,5,6,7,7A-hexahydro-4,7-methano-1H-inden-5/6-yl propinoate (Cyclaprop), 3A,4,5,6,7,7A-hexahydro-4,7-methano-1G-inden-5/6-yl butyrate (Cyclobutanate), 1-(2,6,6-trimethyl-3-cyclohexen-1-yl)-2-buten-1-one (Delta Damascone), 3-(4-ethylphenyl)-2,2-dimethyl propanenitrile (Fleuranil), 3-(O/P-ethylphenyl) 2,2-dimethyl propionaldehyde (Floralozone), tetrahydro-4-methyl-2-(2-methylpropyl)-2H-pyran-4-ol (Floriffol), 1,3,4,6,7,8-hexahydro-4,6,6,7,8,8-hexamethylcyclopenta-gamma-2-benzopyran (Galaxolide), 1-(5,5-dimethyl-1-cyclohexen-1-yl)pent-4-en-1-one (Galbascone), E/Z-3,7-dimethyl-2,6-octadien-1-yl acetate (Geranyl Acetate), α-methyl-1,3-benzodioxole-5-propanal (Helional), 1-(2,6,6-trimethyl-2-cyclohexen-1-yl)-1,6-heptadien-3-one (Hexylon), (Z)-3-hexenyl-2-hydroxybenzoate (Hexenyl Salicylate, CIS-3), 4-(2,6,6-trimethyl-2-cyclohexen-1-yl)-3-buten-2-one (Ionone α), 1-(1,2,3,4,5,6,7,8-octahydro-2,3,8,8-tetramethyl-2-naphthalenyl)-ethan-1-one (Iso E Super), methyl 3-oxo-2-pentylcyclopentaneacetate (Kharismal), 2,2,4-trimethyl-4-phenyl-butanenitrile (Khusinil), 3,4,5,6,6-pentamethylhept-3-en-2-one (Koavone), 3/4-(4-hydroxy-4-methyl-pentyl)cyclohexene-1-carboxaldehyde (Lyral), 3-methyl-4-(2,6,6-trimethyl-2-cyclohexen-1-yl)-3-buten-2-one (Methyl Ionone γ), 1-(2,6,6-trimethyl-2-cyclohexen-1-yl) pent-1-en-3-one (Methyl Ionone α Extra, Methyl Ionone N), 3-methyl-4-phenylbutan-2-ol (Muguesia), cyclopentadec-4-en-1-one (Musk Z4), 3,3,4,5,5-pentamethyl-11,13-dioxatricyclo[7.4.0.0<2,6>]tridec-2(6)-ene (Nebulone), 3,7-dimethyl-2,6-octadien-1-yl acetate (Neryl Acetate), 3,7-dimethyl-1,3,6-octatriene (Ocimene), ortho-tolylethanol (Peomosa), 3-methyl-5-phenylpentanol (Phenoxanol), 1-methyl-4-(4-methyl-3-pentenyl)cyclohex-3-ene-1-carboxaldehyde (Precyclemone B), 2-ethyl-4-(2,2,3-trimethyl-3-cyclopenten-1-yl)-2-buten-1-ol (Sanjinol), 2-methyl-4-(2,2,3-trimethyl-3-cyclopenten-1-yl)-2-buten-1-ol (Santaliff), Terpineol, 2,4-dimethyl-3-cyclohexene-1-carboxaldehyde (Triplal), decahydro-2,6,6,7,8,8-hexamethyl-2H-indeno[4,5-B]furan (Trisamber), 2-tert-butylcyclohexyl acetate (Verdox), 4-tert-butylcyclohexyL acetate (Vertenex), acetyl cedrene (Vertofix), 3,6/4,6-dimethylcyclohex-3-ene-1-carboxaldehyde (Vertoliff), and (3Z)-1-[(2-methyl-2-propenyl)oxy]-3-hexene (Vivaldie).

The terms "fragrance formulation", "fragrance composition", and "perfume composition" mean the same and refer to a consumer composition that is a mixture of compounds including, for example, alcohols, aldehydes, ketones, esters, ethers, lactones, nitriles, natural oils, synthetic oils, and mercaptans, which are admixed so that the combined odors of the individual components produce a pleasant or desired fragrance. The fragrance formulation of the present invention is a consumer composition comprising a compound of the present invention. The fragrance formulation of the present invention may comprise a compound of the present invention and further a complementary fragrance compound as defined above.

The term "fragrance product" means a consumer product that adds a fragrance or masks a malodor. Fragrance products may include, for example, perfumes, colognes, personal care products such as soaps, shower gels, and hair care products, fabric products, air fresheners, cosmetic preparations, and perfume cleaning agents such as detergents, dishwashing materials, scrubbing compositions, and window cleaners. The fragrance product of the present invention is a consumer product that contains a compound of the present invention. The fragrance product of the present invention may contain a compound of the present invention and further a complementary fragrance compound as defined above.

The term "improving" in the phrase "improving, enhancing or modifying a fragrance formulation" is understood to mean raising the fragrance formulation to a more desirable character. The term "enhancing" is understood to mean making the fragrance formulation greater in effectiveness or providing the fragrance formulation with an improved character. The term "modifying" is understood to mean providing the fragrance formulation with a change in character.

Olfactory acceptable amount is understood to mean the amount of compound in perfume compositions the individual component will contribute to its particular olfactory characteristics, but the olfactory effect of the perfume composition will be the sum of the effects of each of the perfumes or fragrance ingredients. Thus the compounds of the invention can be used to alter the aroma characteristics of the perfume composition, or by modifying the olfactory reaction contributed by another ingredient in the composition. The amount will vary depending on many factors including other ingredients, their relative amounts and the effect that is desired.

The amount of the compound of the present invention employed in a fragrance formulation varies from about 0.005 to about 50 weight percent, preferably from 0.1 to about 25 weight percent, and more preferably from about 0.5 to about 10 weight percent. Those with skill in the art will be able to employ the desired amount to provide desired fragrance effect and intensity. In addition to the compounds of the present invention, other materials can also be used in conjunction with the fragrance formulation. Well known materials such as surfactants, emulsifiers, polymers to encapsulate the fragrance can also be employed without departing from the scope of the present invention.

When used in a fragrance formulation this ingredient provides fruity and woody notes that make the fragrance formulation more desirable and noticeable and add the perception of value. All of the odor qualities found in this material assist in beautifying and enhancing the finished accord improving the performance of the other materials in the fragrance. The fruity side is found in many fragrances today which happens to be very trendy, especially for the younger consumers.

The following are provided as specific embodiments of the present invention. Other modifications of this invention will be readily apparent to those skilled in the art. Such modifications are understood to be within the scope of this invention. The chemical materials used in the preparation of the compounds of the present invention are commercially available from Aldrich Chemical Company. As used herein all percentages are weight percent unless otherwise noted, ppm is understood to stand for parts per million, M is understood to be molar, L is understood to be liter, mL is understood to be milliliter, Kg is understood to be kilogram, g be gram, psi is understood to be pound-force per square inch, and mmHg is understood to be millimeters of mercury. IFF as used in the examples is understood to mean International Flavors & Fragrances Inc., New York, N.Y., USA.

EXAMPLE I

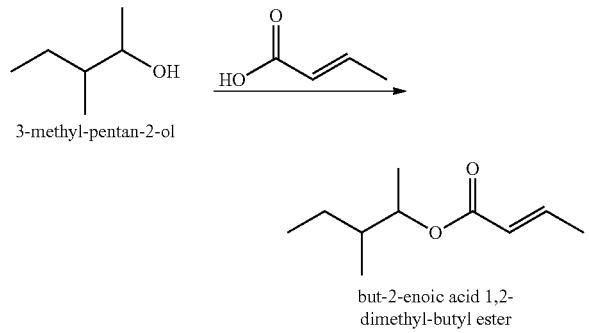

Preparation of But-2-enoic acid 1,2-dimethyl-butyl ester (Structure I)

3-Methyl-pentan-2-ol (400 g), crotonic acid (CH$_3$CH═CHCOOH) (445.5 g), toluene (400 mL), and para-toluenesulfonic acid (PTSA) (4 g) were charged into to 2-L reaction flask fitted with a mechanical stirrer, a thermocouple, a condenser, and a Bidwell-Sterling trap. The reaction mixture was heated to reflux. Water was collected and removed via the Bidwell-Sterling trap. The reaction mixture was aged for about 3.5 hours. The resulting reaction mixture was then cooled and washed sequentially with water, aqueous sodium hydroxide (NaOH) (10%), and brine. The aqueous and organic layers were split. The organic layer was fractional distilled to provide but-2-enoic acid 1,2-dimethyl-butyl ester (444 g) with a boiling point of 106° C. at 34 mmHg.

$^1$H NMR (CDCl$_3$, 400 MHz): 0.9 ppm (m, 6H), 1.2 ppm (m, 4H), 1.4-1.7 ppm (m, 2H), 1.85 ppm (s, 3H), 4.90 ppm (m, 1H), 5.85 ppm (m, 1H), 6.95 ppm (m, 1H)

EXAMPLE II

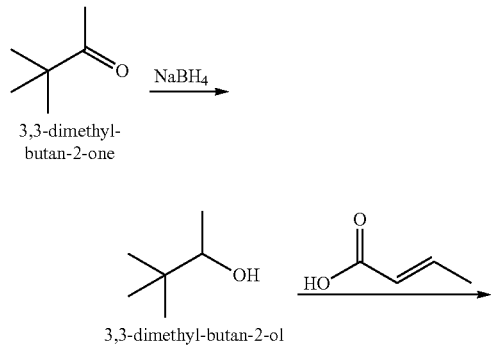

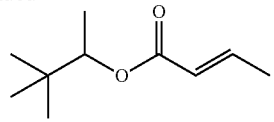

but-2-enoic acid 1,2,2-trimethyl-propyl ester

Preparation of But-2-enoic acid 1,2,2-trimethyl-propyl ester (Structure II)

A reaction flask was charged with 3,3-dimethyl-butan-2-one (200 g) and methanol (200 mL). Sodium borohydride (NaBH$_4$) (22.7 g) was subsequently added slowly over about 30 minutes while the temperature was kept under 40° C. The reaction mixture was aged to room temperature over about 2.5 hours and then poured into a mixture of ice and acetic acid (CH$_3$COOH) (45 g). Hexanes (C$_6$H$_{14}$) (300 mL) were added and aqueous and organic layers were split. The organic layer containing 3,3-dimethyl-butan-2-ol was separated and charged together with crotonic acid (172 g), toluene (300 mL), and PTSA (3 g) into to 2-L reaction flask fitted with a Bidwell-Sterling trap. The reaction mixture was heated to reflux to remove hexanes. Water was collected and removed via the Bidwell-Sterling trap. The reaction mixture was aged at reflux for about 38 hours till GC analysis showed completion of the reaction. The resulting reaction mixture was washed sequentially with brine, sodium bicarbonate (NaHCO$_3$), and brine, and further purified by fractional distillation to provide but-2-enoic acid 1,2,2-trimethyl-propyl ester (176 g) with a boiling point of 66° C. at 0.72 mmHg.

$^1$H NMR (CDCl$_3$, 500 MHz): 6.91-6.99 ppm (m, 1H), 5.84 ppm (d, 1H, J=15.51 Hz, of d, J=1.45 Hz), 4.74 ppm (q, 1H, J=6.37 Hz), 1.88 ppm (d, 3H, J=6.85 Hz, of d, J=1.45 Hz), 1.15 ppm (d, 3H, J=6.40 Hz), 0.92 ppm (s, 9H).

EXAMPLE III

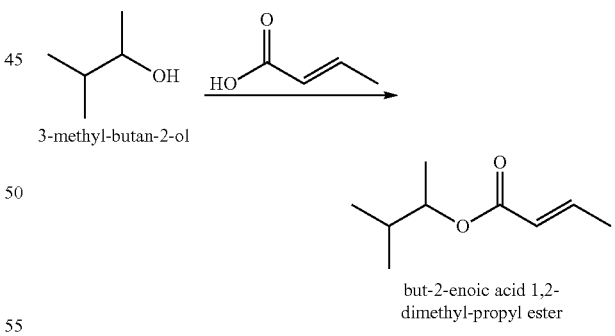

Preparation of But-2-enoic acid 1,2-dimethyl-propyl ester (Structure III)

3-Methyl-butan-2-ol (180 g), crotonic acid (165 g), toluene (200 mL), and PTSA (8 g) were charged into to a 2-L reaction flask fitted with a Bidwell-Sterling trap. The reaction mixture was heated to reflux. Water was collected and removed via the Bidwell-Sterling trap. The reaction mixture was aged at reflux for about 13-15 hours till GC analysis showed completion of the reaction. The resulting reaction mixture was washed sequentially with brine, sodium carbonate ($Na_2CO_3$), and brine, and further purified by fractional distillation to provide but-2-enoic acid 1,2-dimethyl-propyl ester (157 g) with a boiling point of 53° C. at 0.77 mmHg.

$^1$H NMR ($CDCl_3$, 400 MHz): 6.95 ppm (d, 1H, J=15.53 Hz, of q, J=6.90), 5.84 ppm (d, 1H, J=15.53 Hz, of q, J=1.70 Hz), 4.79 ppm (pentet, 1H, J=6.23 Hz), 1.87 ppm (d, 3H, J=6.92 Hz, of d, J=1.72 Hz), 1.75-1.85 ppm (m, 1H), 1.18 ppm (d, 3H, J=6.36 Hz), 0.91 ppm (d, 6H, J=6.84 Hz).

EXAMPLE IV

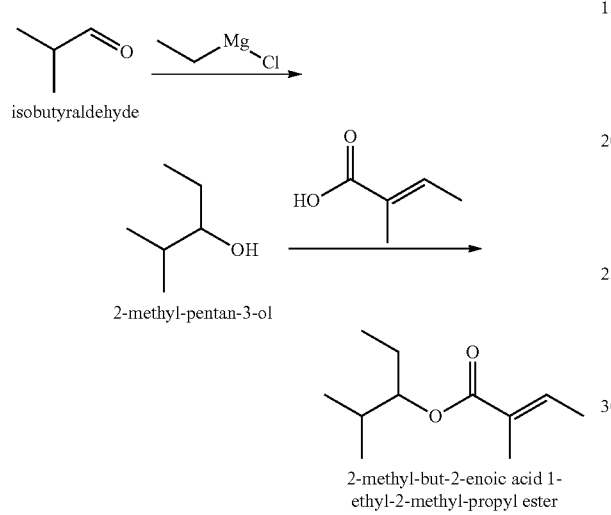

2-methyl-but-2-enoic acid 1-ethyl-2-methyl-propyl ester

Preparation of 2-Methyl-but-2-enoic acid 1-ethyl-2-methyl-propyl ester (Structure IV)

A reaction flask was charged with ethylmagnesium chloride ($CH_3CH_2MgCl$) (2 M, 2.17 L) and cooled to −10° C. Isobutyraldehyde (($CH_3$)$_2$CHCHO) (295 g) was fed over about 1 hour while the temperature was kept under 15° C. The reaction mixture was aged to room temperature over about 6 hours and then poured into a mixture of ice and acetic acid (293 g). Hexanes (350 mL) were added and aqueous and organic layers were split. The organic layer was separated, washed sequentially with sodium bicarbonate ($NaHCO_3$), brine, and water, and further distilled to provide 2-methyl-pentan-3-ol (336 g). 2-Methyl-pentan-3-ol (153 g), 2-methyl-but-2-enoic acid (100 g), toluene (200 mL), and PTSA (8 g) were charged into to 2-L reaction flask fitted with a Dean-Stark trap. The reaction mixture was heated to reflux at about 120° C. Water was removed. The reaction mixture was aged at reflux for about 13-14 hours till GC analysis showed completion of the reaction. The resulting reaction mixture was washed sequentially with sodium bicarbonate and brine, and further purified by fractional distillation to provide 2-methyl-but-2-enoic acid 1-ethyl-2-methyl-propyl ester (81 g) with a boiling point of 91° C. at 1.1 mmHg.

$^1$H NMR ($CDCl_3$, 400 MHz): 6.86 ppm (q, 1H, J=7.04 Hz, of t, J=0.70), 4.74 ppm (d, 1H, J=7.40 Hz, of t, J=5.32 Hz), 1.84-1.92 ppm (m, 1H), 1.85 ppm (s, 3H), 1.79 ppm (d, 3H, J=7.08 Hz, of t, J=0.91 Hz), 1.53-1.63 ppm (m, 2H), 0.91 ppm (d, 6H, J=6.90 Hz, of d, J=1.92 Hz), 0.88 ppm (t, 3H, J=7.66 Hz).

EXAMPLE V

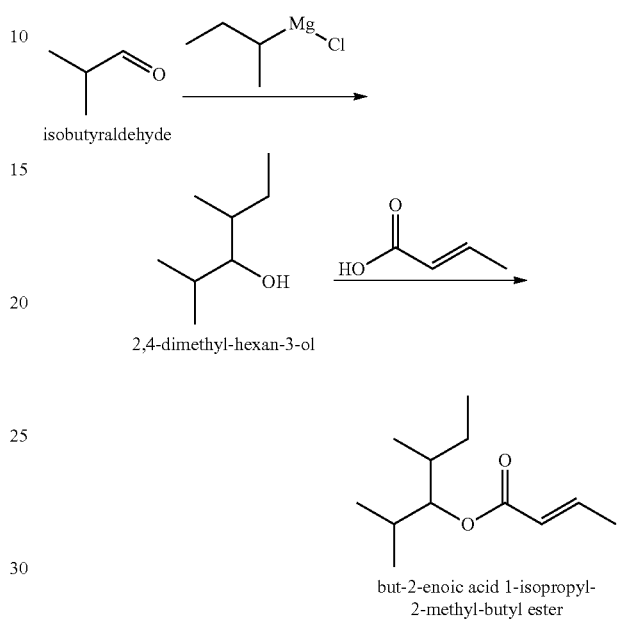

but-2-enoic acid 1-isopropyl-2-methyl-butyl ester

Preparation of But-2-enoic acid 1-isopropyl-2-methyl-butyl ester (Structure V)

A reaction flask was charged with sec-butylmagnesium chloride ($CH_3CH_2CH(CH_3)MgCl$) (2 M, 1.6 L) and cooled to 0° C. sobutyraldehyde (($CH_3$)$_2$CHCHO) (220 g) was fed over about 2 hours while the temperature was kept under 15° C. The reaction mixture was aged to room temperature over about 6 hours and then poured into a mixture of ice and acetic acid (216 g). Hexanes (350 mL) were added and aqueous and organic layers were split. The organic layer was separated and washed sequentially with sodium bicarbonate, brine, and water. The resulting organic layer containing crude 2,4-dimethyl-hexan-3-ol, crotonic acid (387 g), toluene (400 mL), and PTSA (25 g) were then charged into to 3-L reaction flask fitted with a Bidwell-Sterling trap. The reaction mixture was heated to reflux to remove hexanes. Water was collected and removed via the Bidwell-Sterling trap. The reaction mixture was aged at reflux for about 22-30 hours till GC analysis showed completion of the reaction. The resulting reaction mixture was washed sequentially with brine, sodium carbonate (twice), a mixture of sodium hydroxide and sodium carbonate, and brine, rush-over distilled and further fractional distilled to provide but-2-enoic acid 1-isopropyl-2-methyl-butyl ester (186 g) with a boiling point of 100° C. at 0.50 mmHg.

$^1$H NMR ($CDCl_3$, 500 MHz): 6.92-7.00 ppm (m, 1H), 5.86 ppm (d, 1H, J=15.46 Hz), 4.68-4.75 ppm (m, 1H), 1.88-1.97 ppm (m, 1H), 1.87 ppm (d, 3H, J=6.85 Hz), 1.63-1.68 ppm (m, 1H), 1.31-1.51 ppm (m, 1H), 1.05-1.16 ppm (m, 1H), 0.85-0.94 ppm (m, 12H).

EXAMPLE VI

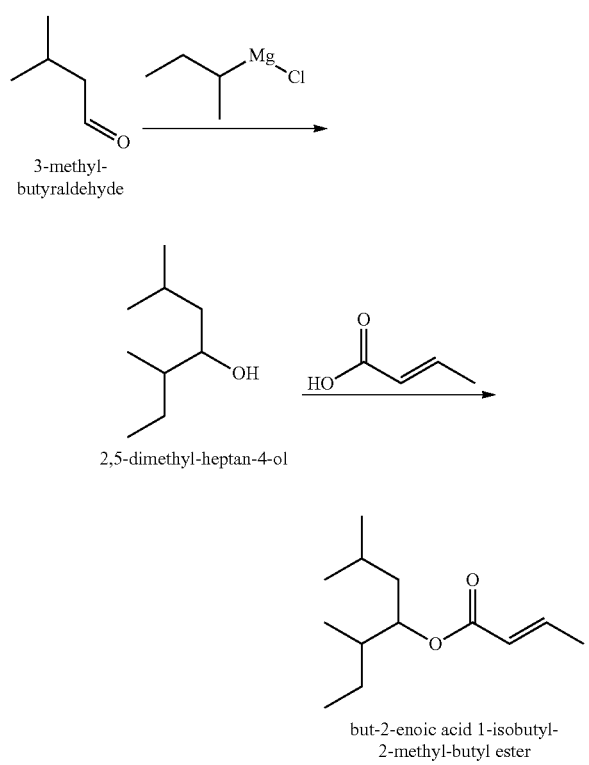

2,5-dimethyl-heptan-4-ol but-2-enoic acid 1-isobutyl-2-methyl-butyl ester

Preparation of But-2-enoic acid
1-isobutyl-2-methyl-butyl ester (Structure VI)

A reaction flask was charged with sec-butylmagnesium chloride (2 M, 1.6 L) and cooled to −10° C. 3-Methyl-butyraldehyde (260 g) was fed over about 2 hours while the temperature was kept under 15° C. The reaction mixture was aged to room temperature over about 6 hours and then poured into a mixture of ice and acetic acid (216 g). Toluene (400 mL) was added and aqueous and organic layers were split. The organic layer was separated and washed sequentially with sodium carbonate, brine, and water. The resulting organic layer containing crude 2,5-dimethyl-heptan-4-ol, crotonic acid (129 g), toluene (150 mL), and PTSA (10 g) were then charged into to 3-L reaction flask fitted with a Bidwell-Sterling trap. The reaction mixture was heated to reflux. Water was collected and removed via the Bidwell-Sterling trap. The reaction mixture was aged at reflux for about 18-20 hours till GC analysis showed completion of the reaction. The resulting reaction mixture was washed sequentially with sodium carbonate (twice) and brine, rush-over distilled and further fractional distilled to provide but-2-enoic acid 1-isobutyl-2-methyl-butyl ester (143 g) with a boiling point of 100° C. at 0.72 mmHg.

$^1$H NMR (CDCl$_3$, 400 MHz): 6.90-7.00 ppm (m, 1H), 5.84 ppm (d, 1H, J=15.53 Hz, of pentet, J=1.60 Hz), 4.96-5.07 ppm (m, 1H), 1.87 ppm (d, 3H, J=6.88 Hz, of d, J=1.68 Hz), 1.38-1.64 ppm (m, 4H), 1.06-1.31 ppm (m, 2H), 0.86-0.95 ppm (m, 12H).

EXAMPLE VII

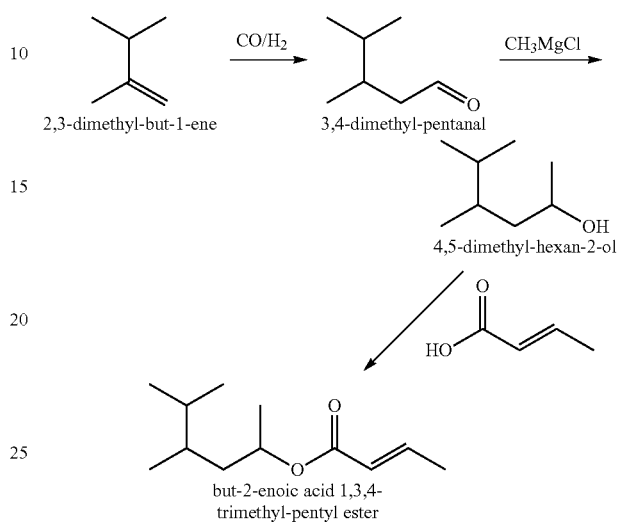

but-2-enoic acid 1,3,4-trimethyl-pentyl ester

Preparation of But-2-enoic acid
1,3,4-trimethyl-pentyl ester (Structure VII)

To prepare 3,4-dimethyl pentanal, 2,3-dimethyl-but-1-ene (1.525 Kg) was loaded into a 4-L ZipperClave® reactor. The pressure was raised to about 300 psi with syngas (a 50/50 mixture of carbon monoxide and hydrogen). The reaction mass was then heated to and kept at about 120° C. for about 10 hours until no further gas absorption. GC analysis determined a conversion rate of about 88%. The resulting organic layer was fractional distilled to provide 3,4-dimethyl pentanal with 98% purity (1.62 Kg) with a boiling point of 102° C. at 150 mmHg.

Methylmagnesium chloride (CH$_3$MgCl) in tetrahydrofuran (THF) (3 M, 1.8 L) was charged into a flame-dried 2-L reaction flask fitted with a mechanical stirrer, a thermocouple, a condenser, and a dropping funnel. The reaction flask was cooled with an external bath to about 15-20° C. 3,4-Dimethyl-pentenal (prepared as above) (422 g) was fed over about 2-3 hours to allow the exotherm temperature at about 30-35° C. After the feeding was completed, the reaction mass was aged for about 2 hours. GC analysis determined a conversion rate of about 96%. The reaction mixture was poured into a mixture of ice and acetic acid (300 g). The organic layer was separated and washed sequentially with brine (500 mL) and sodium carbonate (5%, 300 mL), and further fractional distilled to provide 4,5-dimethyl-hexan-2-ol (410 g) with a boiling point of 114° C. at 90 mmHg.

The obtained 4,5-dimethyl-hexan-2-ol (296 g), crotonic acid (391 g,), PTSA (3 g), and toluene (300 mL) were charged into a 2-L reaction flask fitted with a mechanical stirrer, a thermocouple, a Dean-Stark trap, and a condenser. The reaction mixture was heated to reflux at about 120-130° C. Water was removed azeotropically. The reaction was aged at reflux for about 4-5 hours until no more water evolved. The reaction was cooled to room temperature and quenched with water (400 mL). The organic layer was separated and subsequently washed with sodium carbonate (5%, 300 mL), and further fractional distilled to provide but-2-enoic acid 1,3,4-trimethyl-pentyl ester (241 g) with a boiling point of 108° C. at 13 mmHg.

3,4-Dimethyl Pentanal has the Following NMR Spectral Characteristics:

$^1$H NMR (CDCl$_3$, 500 MHz): 9.76 ppm (t, 1H, J=2.70 Hz), 2.40-2.47 ppm (m, 1H), 2.16-2.23 ppm (m, 1H), 1.96-2.02 ppm (m, 1H), 1.56-1.63 ppm (m, 1H), 0.85-0.93 ppm (m, 9H)

4,5-Dimethyl-hexan-2-ol has the Following NMR Spectral Characteristics:

$^1$H NMR (CDCl$_3$, 500 MHz): 3.79-3.89 ppm (m, 1H), 1.07-1.62 ppm (m, 5H), 1.16 ppm (d, ~50% of 3H, J=6.10 Hz), 1.13 ppm (d, ~50% of 3H, J=6.10 Hz), 0.73-0.87 ppm (m, 9H)

But-2-enoic Acid 1,3,4-trimethyl-pentyl Ester has the Following NMR Spectral Characteristics:

$^1$H NMR (CDCl$_3$, 500 MHz): 6.84-6.99 ppm (m, 1H), 5.78 ppm (d, 1H, J=15.51 Hz), 4.95-5.06 ppm (m, 1H), 1.83 ppm (d, 3H, J=5.90 Hz), 1.30-1.67 ppm (m, 4H), 1.13-1.23 ppm (m, 3H), 0.74-0.86 ppm (m, 9H)

EXAMPLE VIII

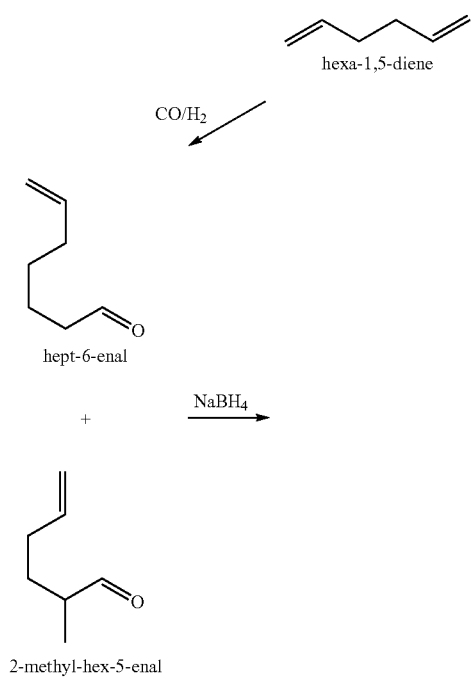

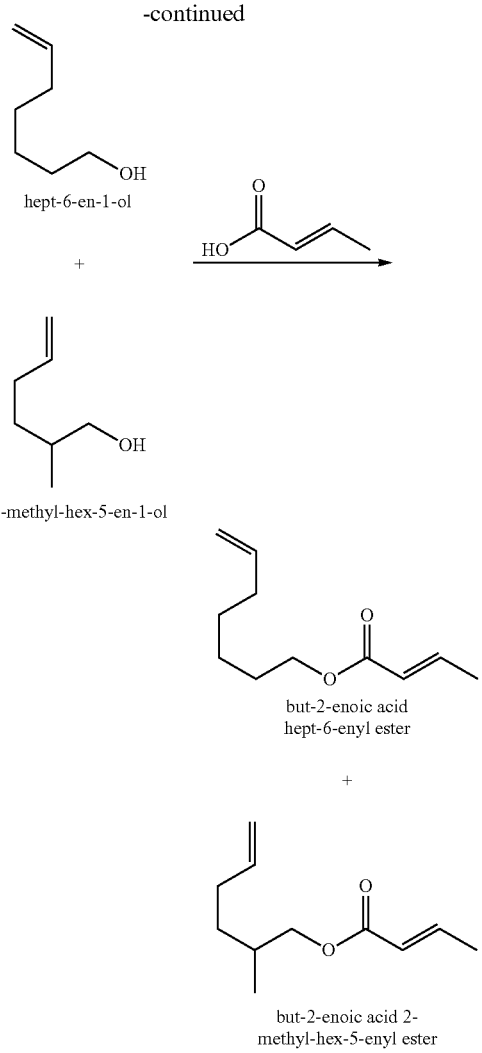

Preparation of But-2-enoic acid hept-6-enyl ester (VIIIa) and But-2-enoic acid 2-methyl-hex-5-enyl ester (VIIIb)

To prepare hept-6-enal and 2-methyl-hex-5-enal, hexa-1,5-diene (995 g) was loaded into a 4-L ZipperClave® reactor. The pressure was raised to about 50 psi with syngas. The reaction mass was then heated to and kept at about 80° C. for about 3-4 hours and GC analysis determined a conversion rate of about 55%. The resulting organic layer was fractional distilled to provide a 65/35 mixture of hept-6-enal and 2-methyl-hex-5-enal (460 g) with a boiling point of 105° C. at 80 mmHg.

Sodium borohydride (36 g) slurried in isopropanol (1.2 L) was charged into a 2-L round bottom flask fitted with a mechanical stirrer, a thermocouple, a condenser, and a dropping funnel. The reaction flask was heated to about 70° C. The mixture of hept-6-enal and 2-methyl-hex-5-enal (prepared as above) (320 g) was fed dropwise into the reaction flask over about 3-4 hours. After the feeding was completed, the reaction mass was aged at 80° C. for about 2 hours. GC analysis determined a conversion rate of greater than 95%. The reaction mixture was cooled, quenched with acetone ((CH$_3$)$_2$CO) (50 mL) by dropwise addition over about 30 minutes, and further quenched with sodium hydroxide (50%, 1 L). The reaction mixture was then distilled at about 95° C. to remove isopropanol atmospherically. The aqueous and organic layers were split. The organic layer was separated and washed with water twice, and further fractional distilled to provide a 65/35 mixture of hept-6-en-1-ol and 2-methyl-hex-5-en-1-ol (194 g) with a boiling point of 88° C. at 21 mmHg The obtained mixture of hept-6-en-1-ol and 2-methyl-hex-5-en-1-ol (172 g), crotonic acid (262 g,), PTSA (2 g), and toluene (150 mL) were charged into a 1-L reaction flask fitted with a mechanical stirrer, a thermocouple, a Dean-Stark trap, and a condenser. The reaction mixture was heated to reflux at about 120-130° C. Water was removed azeotropically. The reaction mixture was aged at reflux for about 2-3 hours until no more water evolved. The resulting reaction mixture was cooled to room temperature and quenched with water (400 mL). The organic layer was separated and subsequently washed with sodium carbonate (5%, 300 mL), and further fractional distilled to provide the 65/35 mixture of but-2-enoic acid hept-6-enyl ester and but-2-enoic acid 2-methyl-hex-5-enyl ester (168 g) with a boiling point of 124° C. at 19 mmHg.

Hept-6-enal has the Following NMR Spectral Characteristics:

$^1$H NMR (CDCl$_3$, 500 MHz): 9.77 ppm (t, 1H, J=1.80 Hz)), 5.72-5.87 ppm (m, 1H), 4.92-5.08 ppm (m, 2H), 2.44 ppm (t, 2H, J=7.40 Hz, of d, J=1.80 Hz), 2.05-2.12 ppm (m, 2H), 1.63-1.67 ppm (m, 2H), 1.40-1.48 ppm (m, 2H)

2-Methyl-hex-5-enal has the Following NMR Spectral Characteristics:

$^1$H NMR (CDCl$_3$, 500 MHz): 9.63 ppm (d, 1H, J=1.85 Hz), 5.72-5.87 ppm (m, 1H), 4.92-5.08 ppm (m, 2H), 2.32-2.45 ppm (m, 1H), 2.00-2.15 ppm (m, 2H), 1.54-1.78 ppm (m, 2H), 1.11 ppm (d, 3H, J=7.05 Hz)

Hept-6-en-1-ol has the Following NMR Spectral Characteristics:

$^1$H NMR (CDCl$_3$, 500 MHz): 5.75-5.87 ppm (m, 1H), 4.91-5.06 ppm (m, 2H), 3.38-3.52 ppm (m, 2H), 2.08-2.22 ppm (m, 2H), 1.25-1.60 ppm (m, 4H), 0.92 ppm (d, 3H, J=6.73 Hz)

2-Methyl-hex-5-en-1-ol has the Following NMR Spectral Characteristics:

$^1$H NMR (CDCl$_3$, 500 MHz): 5.75-5.87 ppm (m, 1H), 4.91-5.06 ppm (m, 2H), 3.58-3.67 ppm (m, 2H), 2.00-2.10 ppm (m, 2H), 1.25-1.60 ppm (m, 7H)

But-2-enoic acid hept-6-enyl Ester has the Following NMR Spectral Characteristics:

$^1$H NMR (CDCl$_3$, 500 MHz): 6.92-7.02 ppm (m, 1H), 5.74-5.88 ppm (m, 2H), 4.92-5.04 ppm (m, 2H), 4.12 ppm (t, 2H, J=6.60 Hz), 2.03-2.08 ppm (m, 2H), 1.85-1.90 ppm (m, 3H), 1.35-1.67 ppm (m, 6H)

But-2-enoic Acid 2-methyl-hex-5-enyl Ester has the Following NMR Spectral Characteristics:

$^1$H NMR (CDCl$_3$, 500 MHz): 6.92-7.02 ppm (m, 1H), 5.74-5.88 ppm (m, 2H), 4.92-5.04 ppm (m, 2H), 3.90-4.04 ppm (m, 2H), 1.95-2.15 ppm (m, 2H), 1.85-1.90 ppm (m, 3H), 1.23-1.68 ppm (m, 3H), 0.95 ppm (d, 3H, J=6.76 Hz)

EXAMPLE IX

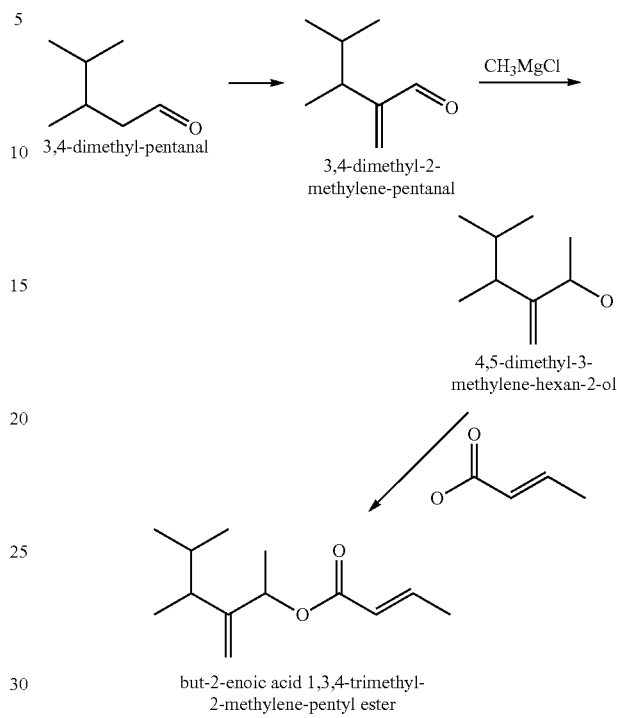

Preparation of But-2-enoic acid 1,3,4-trimethyl-2-methylene-pentyl ester (Structure IX)

To prepare 3,4-dimethyl-2-methylene-pentanal, formaldehyde (CH$_2$O) (37%, 1.081 Kg), acetic acid (58 g), and dibutylamine ((CH$_3$(CH$_2$)$_3$)NH) (105 g) were charged into a 3-L reaction flask fitted with a mechanical stirrer, a thermocouple, a condenser, and a dropping funnel. The reaction mixture was heated to about 70° C. 3,4-Dimethyl-pentanal (prepared as above in EXAMPLE VII) (890 g) was fed dropwise into the reaction mixture over about 3-4 hours. After the feeding was completed, the reaction mixture was aged at about 70° C. for about 6 hours. GC analysis determined a conversion rate of about 90%. The reaction mixture was cooled. The aqueous and organic layers were split. The obtained organic layer was washed with brine (500 mL) and further fractional distilled to provide 3,4-dimethyl-2-methylene-pentanal (834 g) with a boiling point of 85° C. at 60 mmHg.

Methylmagnesium chloride in THF (3 M, 2.65 L) was charged into a flame-dried 2-L reaction flask fitted with a mechanical stirrer, a thermocouple, a condenser, and a dropping funnel. The reaction flask was cooled with an external bath to about 15-20° C. 3,4-Dimethyl-2-methylene-pentenal (prepared as above) (834 g) was fed over about 2-3 hours to allow the exotherm temperature at about 30-35° C. After the feeding was completed, the reaction mass was aged for about 2 hours. GC analysis determined a conversion rate of about 95%. The reaction mixture was poured into a mixture of ice and acetic acid (500 g). The organic layer was separated and washed sequentially with brine (500 mL) and sodium carbonate (5%, 300 mL), and further fractional distilled to provide 4,5-dimethyl-3-methylene-hexan-2-ol (804 g) with a boiling point of 110° C. at 60 mmHg.

The obtained 4,5-dimethyl-3-methylene-hexan-2-ol (280 g), crotonic acid (188 g,), PTSA (2.5 g), and toluene (250 mL) were charged into a 2-L reaction flask fitted with a mechanical stirrer, a thermocouple, a Dean-Stark trap, and a condenser. The reaction mixture was heated to reflux at about 120-130° C. Water was removed azeotropically. The reaction was aged at reflux for about 4-5 hours until no more water evolved. The reaction was cooled to room temperature and quenched with water (400 mL). The organic layer was separated and subsequently washed with sodium carbonate (5%, 300 mL), and further fractional distilled to provide but-2-enoic acid 1,3,4-trimethyl-2-methylene-pentyl ester (290 g) with a boiling point of 114° C. at 11 mmHg.

3,4-Dimethyl-2-methylene-Pentanal has the Following NMR Spectral Characteristics:

$^1$H NMR (CDCl$_3$, 500 MHz): 9.52 ppm (s, 1H), 6.21 ppm (s, 1H), 6.02 ppm (s, 1H), 2.56 ppm (m, 1H), 1.73 ppm (m, 1H), 1.02 ppm (d, 3H, J=7.05 Hz), 0.84 ppm (d, 3H, J=7.01 Hz), 0.83 ppm (d, 3H, J=7.01 Hz)

4,5-Dimethyl-3-methylene-hexan-2-ol has the Following NMR Spectral Characteristics:

$^1$H NMR (CDCl$_3$, 500 MHz): 5.16 ppm (s, ~50% of 1H), 5.12 ppm (s, ~50% of 1H), 4.83 ppm (s, ~50% of 1H), 4.82 ppm (s, ~50% of 1H), 4.17-4.26 ppm (m, 1H), 1.61-1.95 ppm (m, 2H), 1.37-1.48 ppm (m, 1H), 1.30 ppm (d, ~50% of 3H, J=6.40 Hz), 1.28 ppm (d, ~50% of 3H, J=6.45 Hz), 1.01 ppm (t, 3H, J=6.83 Hz), 0.86-0.91 (m, 6H)

But-2-enoic acid 1,3,4-trimethyl-2-methylene-pentyl Ester has the Following NMR Spectral Characteristics:

$^1$H NMR (CDCl$_3$, 500 MHz): 6.85-7.02 ppm (m, 1H), 5.79-5.86 ppm (m, 1H), 5.24-5.40 ppm (m, 1H), 5.14 (s, ~50% of 1H), 5.11 ppm (s, ~50% of 1H), 4.89 ppm (s, ~50% of 1H), 4.85 ppm (s, ~50% of 1H), 1.81-1.92 ppm (m, 4H), 1.63-1.76 ppm (m, 1H), 1.30-1.37 ppm (m, 3H), 0.97-1.14 ppm (m, 3H), 0.81-0.93 ppm (m, 6H)

EXAMPLE X

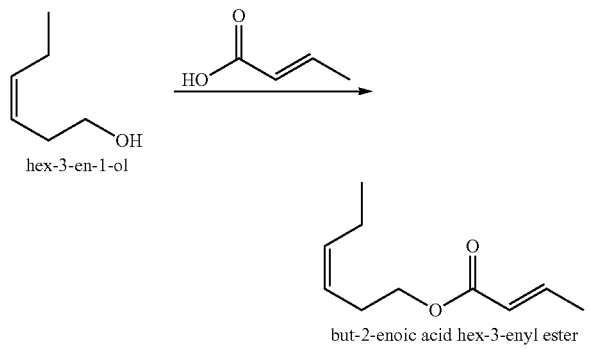

hex-3-en-1-ol but-2-enoic acid hex-3-enyl ester

Preparation of But-2-enoic acid hex-3-enyl ester (Structure X)

Hex-3-en-1-ol (179 g), crotonic acid (181 g), PTSA (7.2 g), and toluene (250 mL) were charged into a 2-L reaction flask fitted with a mechanical stirrer, a thermocouple, a Dean-Stark trap, and a condenser. The reaction mixture was heated to reflux at about 120-130° C. Water was removed azeotropically. The reaction was aged at reflux for about 4-5 hours until no more water evolved. The reaction mixture was cooled to room temperature and quenched with water (400 mL). The organic layer was separated and subsequently washed with sodium carbonate (5%, 300 mL), and further distilled to provide but-2-enoic acid hex-3-enyl ester (247 g) with a boiling point of 109° C. at 20 mmHg.

$^1$H NMR (CDCl$_3$, 500 MHz): 6.97 ppm (d, 1H, J=15.45 Hz, of q, J=6.92 Hz), 5.84 ppm (d, 1H, J=15.45 Hz, of q, J=1.72 Hz), 5.46-5.55 ppm (m, 1H), 5.29-5.37 ppm (m, 1H), 4.12 ppm (t, 2H, J=6.92 Hz), 2.37-2.43 ppm (m, 2H), 2.02-2.11 ppm (m, 2H), 1.87 ppm (d, 3H, J=6.92 Hz, of d, J=1.72 Hz), 0.97 ppm (t, 3H, J=7.54 Hz)

EXAMPLE XI

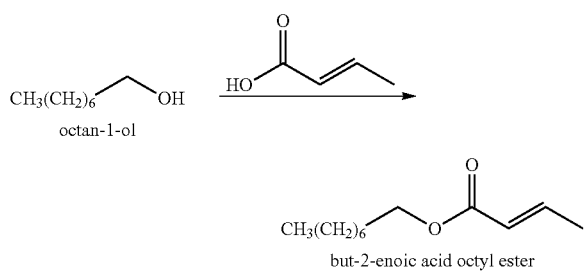

octan-1-ol but-2-enoic acid octyl ester

Preparation of But-2-enoic acid octyl ester (Structure XI)

Octan-1-ol (221 g), crotonic acid (194 g), PTSA (6.4 g), and toluene (300 mL) were charged into a 2-L reaction flask fitted with a mechanical stirrer, a thermocouple, a Dean-Stark trap, and a condenser. The reaction mixture was heated to reflux at about 120-130° C. Water was removed azeotropically. The reaction was aged at reflux for about 7-8 hours until no more water evolved. The reaction mixture was cooled to room temperature and quenched with water (400 mL). The organic layer was separated and subsequently washed with sodium carbonate (5%, 300 mL), and further fractional distilled to provide but-2-enoic acid octyl ester (273 g) with a boiling point of 123° C. at 11 mmHg.

$^1$H NMR (CDCl$_3$, 500 MHz): 6.96 ppm (d, 1H, J=15.52 Hz, of q, J=6.92 Hz), 5.84 ppm (d, 1H, J=15.52 Hz, of q, J=1.66 Hz), 4.11 ppm (t, 2H, J=6.74 Hz), 1.87 ppm (d, 3H, J=6.92 Hz, of d, J=1.66 Hz), 1.60-1.70 ppm (m, 2H), 1.23-1.42 ppm (m, 10H), 0.88 ppm (t, 3H, J=6.84 Hz)

EXAMPLE XII

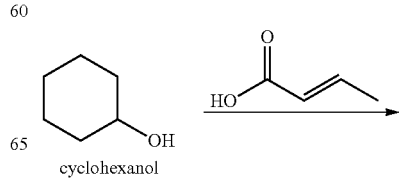

cyclohexanol

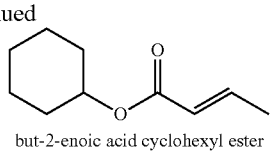

but-2-enoic acid cyclohexyl ester

Preparation of But-2-enoic acid cyclohexyl ester (Structure XII)

Cyclohexanol (220 g), crotonic acid (199 g), PTSA (8 g), and toluene (300 mL) were charged into a 2-L reaction flask fitted with a mechanical stirrer, a thermocouple, a Dean-Stark trap, and a condenser. The reaction mixture was heated to reflux at about 120-130° C. Water was removed azeotropically. The reaction was aged at reflux for about 4-5 hours until no more water evolved. The reaction mixture was cooled to room temperature and quenched with water (400 mL). The organic layer was separated and subsequently washed with sodium carbonate (5%, 300 mL), and further fractional distilled to provide but-2-enoic acid cyclohexyl ester (290 g) with a boiling point of 104° C. at 13 mmHg.

$^1$H NMR (CDCl$_3$, 500 MHz): 6.95 ppm (d, 1H, J=15.45 Hz, of q, J=6.92 Hz), 5.83 ppm (d, 1H, J=15.45 Hz, of q, J=1.48 Hz), 4.77-4.88 ppm (m, 1H), 1.87 ppm (d, 3H, J=6.92 Hz, of d, J=1.48 Hz), 1.20-1.92 ppm (m, 10H)

EXAMPLE XIII

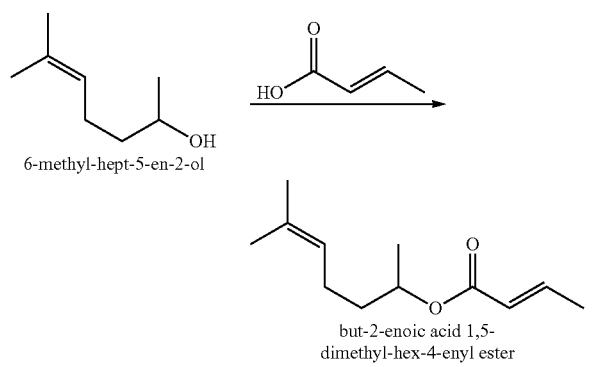

6-methyl-hept-5-en-2-ol but-2-enoic acid 1,5-dimethyl-hex-4-enyl ester

Preparation of But-2-enoic acid 1,5-dimethyl-hex-4-enyl ester (Structure XIII)

6-Methyl-hept-5-en-2-ol (256 g, commercially available at IFF), crotonic acid (193 g), PTSA (2.5 g), and toluene (250 mL) were charged into a 2-L reaction flask fitted with a mechanical stirrer, a thermocouple, a Dean-Stark trap, and a condenser. The reaction mixture was heated to reflux at about 110-133° C. Water was removed azeotropically. The reaction was aged at reflux for about 6 hours until no more water evolved. The reaction mixture was cooled to under 60° C. and quenched with water (300 mL). The aqueous and organic layers were split. The organic layer was subsequently washed with sodium carbonate (2%, 300 mL) and further fractional distilled to provide but-2-enoic acid 1,5-dimethyl-hex-4-enyl ester (204 g) with a boiling point of 98° C. at 4 mmHg.

$^1$H NMR (CDCl$_3$, 500 MHz): 6.94 ppm (d, 1H, J=15.50 Hz, of q, J=6.85 Hz), 5.83 ppm (d, 1H, J=15.5 Hz), 5.03-5.15 ppm (m, 1H), 4.89-5.12 ppm (m, 1H), 1.97-2.05 ppm (m, 2H), 1.87 ppm (d, 3H, J=6.85 Hz), 1.67 ppm (s, 3H), 1.58 ppm (s, 3H), 1.46-1.72 ppm (m, 2H), 1.23 ppm (d, 3H, J=6.80 Hz)

EXAMPLE XIV

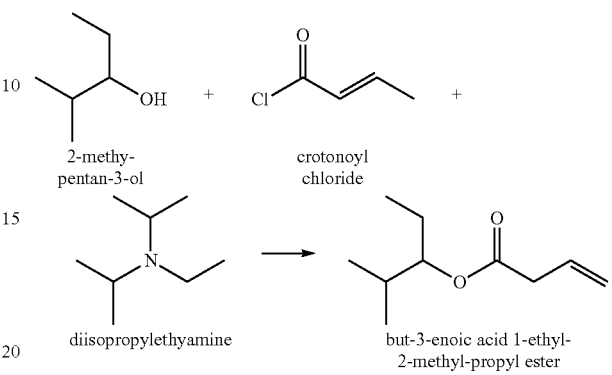

2-methyl-pentan-3-ol crotonoyl chloride diisopropylethyamine but-3-enoic acid 1-ethyl-2-methyl-propyl ester Preparation of But-3-enoic acid 1-ethyl-2-methyl-propyl ester (Structure XIV)

Crotonoyl chloride (21.5 g) in dichloromethane (CH$_2$Cl$_2$) (100 mL) was charged into a 2-L reaction flask and cooled to 0° C. 2-Methyl-pentan-3-ol (prepared as above in EXAMPLE IV) (21 g) was added followed by diisopropylethylamine (31.9 g). The reaction mixture was aged at about 0-10° C. for about 30 minutes and poured into dilute hydrochloric acid (HCl) (33 g in 170 g water). Hexanes were added and the aqueous and organic layers were split. The organic layer was separated and subsequently purified via liquid chromatography to provide but-3-enoic acid 1-ethyl-2-methyl-propyl ester (28 g).

$^1$H NMR (CDCl$_3$, 500 MHz): 5.90-6.00 ppm (m, 1H), 5.14-5.20 ppm (m, 2H), 4.67-4.72 ppm (m, 1H), 3.10 ppm (d, 2H, J=6.95 Hz, of t, J=1.44 Hz), 1.80-1.87 pm (m, 1H), 1.50-1.62 ppm (m, 2H), 0.89 ppm (d, 6H, J=6.60 Hz), 0.87 ppm (t, 3H, J=7.35 Hz).

EXAMPLE XV

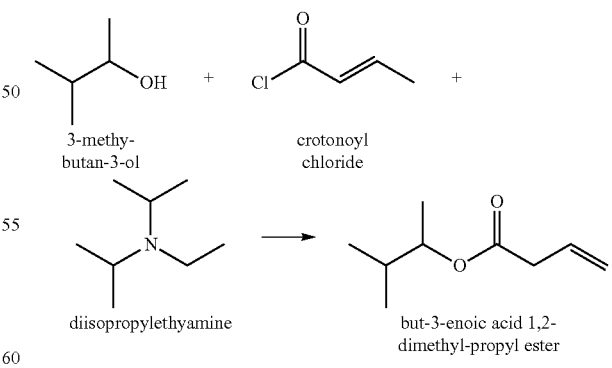

3-methyl-butan-3-ol crotonoyl chloride diisopropylethyamine but-3-enoic acid 1,2-dimethyl-propyl ester Preparation of But-2-enoic acid 1,2-dimethyl-propyl ester (Structure XV)

Crotonoyl chloride (21.35 g) in dichloromethane (100 mL) was charged into a 2-L reaction flask and cooled to 0° C.

3-Methyl-butan-2-ol (18 g) was added followed by diisopropylethylamine (31.7 g). The reaction mixture was aged at 0-10° C. for about 30 minutes and poured into dilute hydrochloric acid (33 g in 170 g water). Hexanes were added and the aqueous and organic layers were split. The organic layer was separated and subsequently purified via liquid chromatography to provide but-2-enoic acid 1,2-dimethyl-propyl ester (25.6 g).

$^1$H NMR (CDCl$_3$, 400 MHz): 5.88-5.99 ppm (m, 1H), 5.13-5.20 ppm (m, 2H), 4.75 ppm (pentet, 1H, J=6.25 Hz), 3.08 ppm (d, 2H, J=6.96 Hz, of t, J=1.34 Hz), 1.76 ppm (octet, 1H, J=6.77 Hz), 1.16 ppm (d, 3H, J=6.36 Hz), 0.90 ppm (d, 6H, J=6.84 Hz).

EXAMPLE XVI

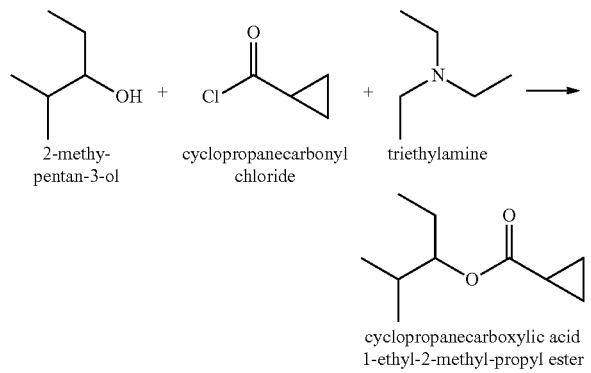

2-methyl-pentan-3-ol + cyclopropanecarbonyl chloride + triethylamine → cyclopropanecarboxylic acid 1-ethyl-2-methyl-propyl ester

Preparation of Cyclopropanecarboxylic acid 1-ethyl-2-methyl-propyl ester (Structure XVI)

2-Methyl-penta-3-nol (20 g), cyclopropanecarbonyl chloride (22.5 g), and toluene (50 mL) were charged into a 250-mL reaction flask at ambient temperature. Triethylamine (23.97 g) was fed into the reaction mixture for over 10 minutes to allow the exotherm temperature of about 21-46° C. during the feeding. The temperature reached and stabilized at about 46° C. when the feeding was completed. The reaction mixture was then heated to about 80° C. Temperature reached about 106° C. after 10 minutes. Hexanes (30 mL) were added. The aqueous and organic layers were split. The organic layer was washed twice with brine and further purified with liquid chromatography to provide cyclopropanecarboxylic acid 1-ethyl-2-methyl-propyl ester (26.6 g).

$^1$H NMR (CDCl$_3$, 500 MHz): 4.64-4.69 ppm (m, 1H), 1.82 ppm (sextet, 1H, J=6.78 Hz), 1.49-1.65 (m, 3H), 0.96-1.01 ppm (m, 2H), 0.81-0.90 ppm (m, 11H).

EXAMPLE XVII

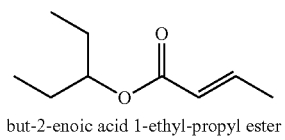

but-2-enoic acid 1-ethyl-propyl ester

Preparation of But-2-enoic acid 1-ethyl-propyl ester (Structure XVII)

But-2-enoic acid 1-ethyl-propyl ester was similarly prepared.

$^1$H NMR (CDCl$_3$, 400 MHz): 6.96 ppm (d, 1H, J=15.51 Hz, of q, J=6.90 Hz), 5.85 ppm (d, 1H, J=15.51 Hz, of q, J=1.66 Hz), 4.81 ppm (pentet, 1H, J=6.19 Hz), 1.88 ppm (d, 3H, J=6.88 Hz, of d, J=1.64 Hz), 1.52-1.65 ppm (m, 4H), 0.89 ppm (t, 6H, J=7.44 Hz).

EXAMPLE XVIII

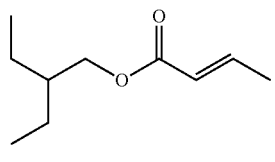

but-2-enoic acid 2-ethyl-butyl ester

Preparation of But-2-enoic acid 2-ethyl-butyl ester (Structure XVIII)

But-2-enoic acid 2-ethyl-butyl ester was similarly prepared.

$^1$H NMR (CDCl$_3$, 400 MHz): 6.95 ppm (d, 1H, J=15.55 Hz, of q, J=6.89 Hz), 5.84 ppm (d, 1H, J=15.55 Hz, of q, J=1.69 Hz), 4.05 ppm (t, 2H, J=5.84 Hz), 1.88 ppm (d, 3H, J=6.92 Hz, of d, J=1.72 Hz), 1.54 ppm (pentet, 1H, J=6.28 Hz), 1.37 ppm (pentet, 4H, J=7.20 Hz), 0.90 ppm (t, 6H, J=7.46 Hz).

EXAMPLE XIX

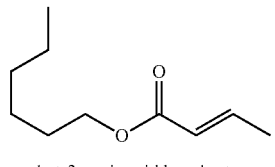

but-2-enoic acid hexyl ester

Preparation of But-2-enoic acid hexyl ester (Structure XIX)

But-2-enoic acid hexyl ester was similarly prepared.

$^1$H NMR (CDCl$_3$, 400 MHz): 6.96 ppm (d, 1H, J=15.53 Hz, of q, J=6.91 Hz), 5.84 ppm (d, 1H, J=15.53 Hz, of q, J=1.72 Hz), 4.11 ppm (t, 2H, J=6.74 Hz), 1.87 ppm (d, 3H, J=6.92 Hz, of d, J=1.72 Hz), 1.64 ppm (pentet, 2H, J=6.80 Hz), 1.27-1.41 ppm (m, 6H), 0.89 ppm (t, 3H, J=6.94 Hz).

EXAMPLE XX

The fragrance properties of the above compounds (i.e., Structures I-XIX) were evaluated using (i) odor strength of 0 to 10, where 0=none, 1=very weak, 5=moderate, 10=extremely strong; and (ii) level of complexity, where 0=none, 1=very low, 5=moderate, 10=extremely high. Averaged scores are reported in the following:

| Chemical Name | Compound | Odor Profile | Strength | Complexity |
| --- | --- | --- | --- | --- |
| But-2-enoic acid 1,2-dimethyl-butyl ester (Structure I) | | Strong and complex with fruity and sweet combination, woody winey, creamy, and spicy with cumin curry notes. | 8 | 8 |
| But-2-enoic acid 1,2,2-trimethyl-propyl ester (Structure II) | | Fruity, sweet, slightly hay-like, and slightly metallic. | 5 | 4 |
| But-2-enoic acid 1,2-dimethyl-propyl ester (Structure III) | | Fruity, winey, woody, green, slightly dirty and animalic. | 7 | 5 |
| But-2-enoic acid 1-ethyl-propyl ester (Structure XVII) | | Fatty, oily, fishy, dirty, and chemical. | 5 | 5 |
| But-2-enoic acid 2-ethyl-butyl ester (Structure XVIII) | | Fruity, sweet, woody, floral, green, and weak. | 4 | 4 |
| But-2-enoic acid hexyl ester (Structure XIX) | | Fruity, green, chemical, mushroom, and soapy. | 5 | 4 |
| 2-Methyl-but-2-enoic acid 1-ethyl-2-methyl-propyl ester (Structure IV) | | Fruity, woody, chemical, metallic, sour, and kerosene. | 7 | 6 |
| But-2-enoic acid 1-isopropyl-2-methyl-butyl ester (Structure V) | | Fruity, chemical, phenolic, very thin and slightly metallic. | 3 | 3 |
| But-2-enoic acid 1-isobutyl-2-methyl-butyl ester (Structure VI) | | Fruity, winey, floral, sweet, and weak. | 4 | 5 |
| But-2-enoic acid 1,3,4-trimethyl-pentyl ester (Structure VII) | | Fruity, sweet, winey, and weak. | 3 | 5 |

| Chemical Name | Compound | Odor Profile | Strength | Complexity |
|---|---|---|---|---|
| But-2-enoic acid hept-6-enyl ester (Structure VIIIa) But-2-enoic acid 2-methyl-hex-5-enyl ester (Structure VIIIb) | | Fruity, dirty, chemical, and metallic. | 3 | 3 |
| But-2-enoic acid 1,3,4-trimethyl-2-methylene-pentyl ester (Structure IX) | | Fruity with dry hay quality, winey, woody, slightly oily, chemical with aldehydic fatty note. | 6 | 5 |
| But-2-enoic acid hex-3-enyl ester (Structure X) | | Green, fresh, slightly dirty, chemical, and metallic. | 5 | 5 |
| But-2-enoic acid octyl ester (Structure XI) | | Fruity with hay quality, winey with mushroom note, slightly harsh and chemical. | 6 | 7 |
| But-2-enoic acid cyclohexyl ester (Structure XII) | | Fruity, sweet, floral, green, woody, and weak. | 4 | 4 |
| But-2-enoic acid 1,5-dimethyl-hex-4-enyl ester (Structure XIII) | | Fruity, slightly nutty and woody, but dirty, chemical, and slightly harsh. | 4 | 4 |
| But-3-enoic acid 1-ethyl-2-methyl-propyl ester (Structure XIV) | | Fruity and sweet, but dirty and chemical. | 6 | 4 |
| But-3-enoic acid 1,2-dimethyl-propyl ester (Structure XV) | | Fruity with hay quality, less complex and less intense, not appealing. | 7.5 | 7 |
| Cyclopropanecarboxylic acid 1-ethyl-2-methyl-propyl ester (Structure XVI) | | Fruity, woody, aldehydic, winey, green, herbaceous, spicy, but fatty. | 6 | 6 |

Structure I exhibited particularly desirable, strong, and complex odors, superior to Structures II-XIX. Its advantageous properties are unexpected.

What is claimed is:

1. A compound, trans-but-2-enoic acid 1,2-dimethyl-butyl ester.

2. A method of improving, enhancing or modifying a fragrance formulation through the addition of an olfactory acceptable amount of trans-but-2-enoic acid 1,2-dimethyl-butyl ester.

3. The method of claim 2, wherein the fragrance formulation is incorporated into a product selected from the group consisting of a perfume, a cologne, a toilet water, a cosmetic product, a personal care product, a fabric care product, a cleaning product, and an air freshener.

4. The method of claim 2, wherein the cleaning product is selected from the group consisting of a detergent, a dishwashing composition, a scrubbing compound, and a window cleaner.

5. The method of claim 2, wherein the olfactory acceptable amount is from about 0.005 to about 50 weight percent of the fragrance formulation.

6. The method of claim 2, wherein the olfactory acceptable amount is from about 0.1 to about 25 weight percent of the fragrance formulation.

7. The method of claim 2, wherein the olfactory acceptable amount is from about 0.5 to about 10 weight percent of the fragrance formulation.

8. A fragrance formulation containing an olfactory acceptable amount of trans-but-2-enoic acid 1,2-dimethyl-butyl ester.

9. A fragrance product containing an olfactory acceptable amount of the compound of claim 1.

* * * * *